United States Patent

Spahn

(10) Patent No.: US 8,767,920 B2
(45) Date of Patent: Jul. 1, 2014

(54) MEDICAL IMAGING SYSTEM AND ANTI-COLLISION METHOD WITH A CONTROLLABLE ARM

(75) Inventor: Martin Spahn, Chicago, IL (US)

(73) Assignee: Siemens Aktiengesellschaft, München (DE)

( * ) Notice: Subject to any disclaimer, the term of this patent is extended or adjusted under 35 U.S.C. 154(b) by 1888 days.

(21) Appl. No.: 11/580,768

(22) Filed: Oct. 13, 2006

(65) Prior Publication Data

US 2007/0086570 A1 Apr. 19, 2007

(30) Foreign Application Priority Data

Oct. 13, 2005 (DE) .................. 10 2005 049 106

(51) Int. Cl.
*H05G 1/54* (2006.01)

(52) U.S. Cl.
USPC .......................................... 378/117; 378/207

(58) Field of Classification Search
USPC ......................................... 378/193–198, 117
See application file for complete search history.

(56) References Cited

U.S. PATENT DOCUMENTS

| | | | |
|---|---|---|---|
| 4,987,583 A * | 1/1991 | Travanty et al. | 378/91 |
| 5,654,997 A | 8/1997 | Brownell et al. | |
| 6,272,368 B1 | 8/2001 | Alexandrescu | |
| 6,435,715 B1 | 8/2002 | Betz et al. | |
| 6,814,489 B2 * | 11/2004 | Jensen et al. | 378/197 |
| 2001/0005410 A1 * | 6/2001 | Rasche et al. | 378/197 |
| 2004/0258210 A1 * | 12/2004 | Ritter | 378/198 |
| 2005/0054915 A1 * | 3/2005 | Sukovic et al. | 600/424 |
| 2005/0117703 A1 * | 6/2005 | Oota | 378/117 |
| 2005/0171644 A1 * | 8/2005 | Tani | 700/253 |
| 2005/0226377 A1 * | 10/2005 | Wong et al. | 378/65 |
| 2006/0274888 A1 | 12/2006 | Bernhardt et al. | |
| 2007/0279199 A1 * | 12/2007 | Danz et al. | 340/435 |

FOREIGN PATENT DOCUMENTS

| | | |
|---|---|---|
| DE | 43 35 301 C1 | 12/1994 |
| DE | 197 43 500 A1 | 4/1999 |
| DE | 19855213 A1 | 6/2000 |
| DE | 10 2005 012 177 A1 | 10/2005 |
| DE | 10 2004 042 790 A1 | 3/2006 |
| DE | 10 2005 023 165 A1 | 11/2006 |
| EP | 0 395 352 A1 | 10/1990 |
| EP | 1 527 738 A1 | 5/2005 |

OTHER PUBLICATIONS

M. Spahn, V. Heer and R. Freytag, "Flachbilddetektoren in der Röntgendiagnostik", Radiologe 2003, vol. 3, No. 5, pp. 340-350.

* cited by examiner

*Primary Examiner* — Hoon Song

(57) ABSTRACT

The invention relates to a medical imaging system as well as an anti-collision method for the like. With this, the movement of a moveable part, e.g. a C-arm is stopped or slowed down if the part approaches the patient, i.e. falls below a predeterminable minimal distance to specific surface areas of the patient or approaches these. These distances are detected by means of at least one sensor.

4 Claims, 2 Drawing Sheets

MEDICAL IMAGING SYSTEM AND ANTI-COLLISION METHOD WITH A CONTROLLABLE ARM

CROSS REFERENCE TO RELATED APPLICATIONS

This application claims priority of German application No. 10 2005 049 106.5 filed Oct. 13, 2005, which is incorporated by reference herein in its entirety.

FIELD OF THE INVENTION

The invention relates to a medical imaging system with a part which can be moved about a patient and in particular a system, in which the movement of the moveable part is controlled by means of a control device, which stops or slows down the movement, if the part approaches the patient, i.e. it falls below a predeterminable minimal distance to specific surface areas of the patient or approaches these.

BACKGROUND OF THE INVENTION

In the prior art, medical imaging system, in particular x-ray systems, are known, which are characterized by extensive flexibility in the movements of the image recording devices about the patients. In the case of an x-ray system, these moveable parts are in particular the x-ray detector and the x-ray tube. The so-called C-arm x-ray systems, in which the x-ray tube and detector are each affixed to arms of a C-arm opposing one another, are particularly popular, said C-arm being moveable in any manner about the patient in order to enable x-ray recordings from any projection directions. By varying the distance between the x-ray detector and the patient, the magnification and the image-distorting scattered radiation can furthermore be minimized. Such systems, such as for instance the AXIOM Artis by Siemens AG, are used in particular as angiography systems. Quasi-tomographic 3D images are increasingly generated using such x-ray devices, in which the C-arm is moved about the patient at approximately 180°. With such a run, which is also referred to as "Dynarun", the moveable parts are partly rotated about the patient at a considerable speed. One problem with this type of imaging system with moveable parts thus consists in the possibility of a collision of the moveable parts with the patient. To rule out dangers to the patient, protective mechanisms must thus be used.

In the meantime, digital imaging methods play a decisive role within medical diagnostics. Whilst digital techniques were used from the start in diagnostics methods, such as for instance computed tomography, magnetic resonance, ultrasound and nuclear medicine methods, the transition to digital imaging is currently taking place to a great extent, particularly with the aid of surface detectors in "conventional" x-ray methods, such as for instance radiography, mammography, angiography or also cardiology (see Spahn et al. "Digitale Röntgen-Detektoren in der Röntgendiagnostik", [Digital x-ray detectors within x-ray diagnostics], Radiologie 43 (2003), pages 340 to 350 for instance).

These new methods require ever faster acquisitions and/or an ever larger number of images for a three-dimensional image acquisition, with robot arms being used in the meantime in the case of conventional projection radiography for instance, said robot arms being able to be controlled by selecting an organ program and being automatically moved into a new position. It is of interest here to implement the method as quickly as possible, in order to speed up hospital procedures.

The risk here is the possibility of a collision of the moveable part, such as for instance the robot arm, with the patient. The risk of a collision between this support arm and the patient or the support arm and another mechanical component such as the table for instance and a second support arm or other medical devices particularly exists with fast movements of mechanical support arms. Different devices and methods are known here to avoid a collision or to lessen the effect of a collision.

With the above-mentioned system AXIOM Artis, a protective zone encasing the patient is defined for instance. If a C-arm approaches this protective zone, it is considerably slowed down in order to avoid the risk of a collision. This protective zone is the same for all patients and takes the shape of an approximate ellipsoid arranged over the patient support. With patients of low weight in particular, this protective zone is thus often remote from the actual patient surface. It thus often takes an unnecessarily long time to run a specific angulation of the C-arm.

With devices made by the company Philips, capacitive sensors are partly arranged on the C-arm, said sensors detecting the proximity of the patient and thereupon slowing down the movement of the C-arm. These sensors nevertheless only have a minimal coverage, so that the intention here is to slow down the movement of the C-arm when entering an accepted protective zone, as rapid movements can otherwise result in a collision.

Both systems feature mechanical position indicators as a final safety device, which in the event of actual contact with the patient, immediately stop the movement of the moveable parts (cf. also EP 0 395 352 A1, which discloses a decoupling of the arm engine from the power supply in the event of a collision).

One disadvantage with the mechanical design of an anti-collision method or the calculation of a protective zone is that the method is either based on contact or requires significant computing effort, so that with increasingly faster movements of the moveable part, the response time, which is hereby ever shorter, is often insufficient to actually prevent a collision, and/or increasingly higher braking pulses are needed to intercept the moveable part. This in turn requires steadier and more powerful motors and/or braking systems, which in turn increases the costs and the dimensions or the systems, whereby the braking pulses and the course of motion of the moveable part is finally once again negatively influenced.

SUMMARY OF THE INVENTION

The object underlying the invention is to provide a medical imaging system with a faster, more precise and simpler anti-collision system, as a well as a corresponding anti-collision method.

This object is achieved by the invention with the characterizing features of the independent claims. Preferred embodiments of the imaging system according to the invention and the anti-collision method are specified in the respective dependent claims.

In accordance with the invention, the medical imaging system, comprising a moveable part in respect of the patient, such as for instance a C-arm or a robot arm, is equipped with at least one sensor, which detects the surface of the patient or of another object, whilst a control device, which controls the movement of the moveable part, accordingly controls the movement of the moveable part on the basis of the calculated distances between the moveable part and the surface of the patient or another object, in other words, stops it or slows it down for instance, if the part approaches or touches the patient or another object.

The control device advantageously calculates the distances of the moveable part from the surface of the patient or another object lying in the traversing path from the detected surface of the patient, and correspondingly controls the movement. To this end, the at least one sensor transmits the positions of individual surface areas of the patient or another object to the control device and at the same time the control device continuously determines the position of the moveable part and stores this position and/or obtains the position of the moveable part from a second sensor which detects the position of the moveable part and transmits it to the control device. The control device can then determine the distances between the moveable part and the corresponding surface areas from the positions and can correspondingly control the speed and/or the direction of motion of the moveable part.

The sensor for determining the surface areas can be an ultrasound sensor, an optical sensor or an electromagnetic sensor. In particular, sensors based on contact are not used as in the prior art, but instead sensors which can already locate and specify an approximation between a sensor-equipped system component such as for instance the moveable part and external objects such as the patient from the distance. Such sensors are particularly advantageous for rapid movements, such as for instance in the case of 3D acquisition.

The sensors are advantageously integrated into the detector housing of the imaging device or into and/or onto the x-ray tube or other exposed areas of the moveable part.

The second sensor can, according to a further advantageous embodiment of the invention, likewise be an electromagnetic sensor, which is composed of a first sensor part, which generates an electromagnetic field in the space about the patient and/or about the medical imaging system and of a second sensor part, which is attached to the moveable part and detects the position of the moveable part in the electromagnetic field. The second sensor can optionally also be an optical sensor, an acceleration sensor or an ultrasound sensor, which detects the position of the moveable part. Such a second sensor can however optionally be dispensed with, once the control device stores the traversing path of the moveable path by means of a corresponding controller, so that the exact position in the space is always known to the control device after an initial calibration.

Advantageously, the imaging system is an x-ray system and the moveable part is an x-ray detector or an x-ray tube. The imaging system is in particular a C-arm system, in which the x-ray detector and the x-ray tube are affixed to a large C-arm, which can be moved about the patient. According to a further advantageous embodiment of the invention, a number of collision sensors are affixed here to different points on the moveable part.

The coordinate system of the imaging system and that of the sensor or of the sensors are advantageously spatially calibrated in respect of each other. This allows the control device to calculate the distances between the moveable part and the surface areas of the external object, such as for instance the surface of the patient. Furthermore the imaging system can also be designed to create a 3D model of the patient from the detected surface of the patient and to register this with the coordinate system of the imaging system. In this case, the control device can predetermine the movement of the moveable part precisely. This 3D model is advantageously updated at regular intervals, in order to avoid a false 3D model forming the basis of the projections of the control device with the movements of the patient. All calculations can also be carried out by an external computing unit, which supplies the results to the control device.

The present invention furthermore relates to an anti-collision method for a medical imaging system, with a part which can be moved about a patient, for preventing a collision of the moveable part with an external object, such as for instance the patient, with the movement of the moveable part being controllable by a control device as a function of the distance to the patient, in which the surface of the patient is detected by at least one sensor and the control device correspondingly controls the movement of the moveable part on the basis of the calculated distances between the moveable part and the surface of the object.

In the method, the positions of individual surface areas of the object are detected by the at least one sensor and are transmitted to the control device. The positions of the moveable part are continuously stored or detected by means of a second sensor and forwarded to the control device. The control device can then determine the distances between the moveable part and the corresponding surface areas of the patient and/or another object and correspondingly control the speed and/or the direction of motion of the moveable part. According to a preferred embodiment of the invention, the surface detection is enabled by means of an optical sensor, with the coordinate system of the imaging system and that of the optical sensor being calibrated in respect of each other prior to recording the corresponding image data.

BRIEF DESCRIPTION OF THE DRAWINGS

An advantageous embodiment of the invention is described in further detail with reference to the appended drawings, in which.

DETAILED DESCRIPTION OF THE INVENTION

Figure 1:
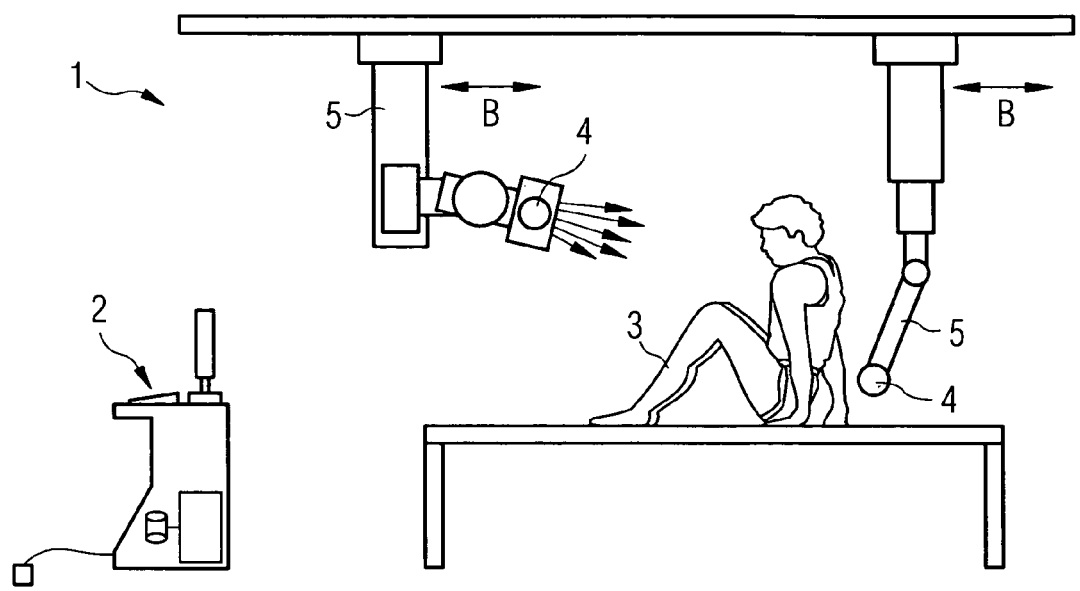
FIG. 1 shows a medical imaging system according to the invention, with collision sensors on exposed points on the moveable parts.

FIG. 1 shows a medical imaging system 1 with a schematically illustrated patient 3, which is positioned on a table. A 3D stand for the x-ray emitter (depicted in the left of the image) and a 3D stand for the x-ray detector are positioned on both sides of the patient, so that fluoroscopy recordings of the lungs of the patient can be produced for instance. For adjustment purposes, both stands can be moved in the direction of motion B or vertically thereto. Furthermore, the x-ray detector can be rotated. This moveable part 5 is provided with a sensor 4, and, similarly to the x-ray emitter, is also equipped with a sensor 4. The two sensors 4 allow corresponding distances between the moveable parts 5 and the surface of the patient 3 to be detected, and transmitted to a control device 2, which controls the movement B of the moveable parts 5.

Figure 2:
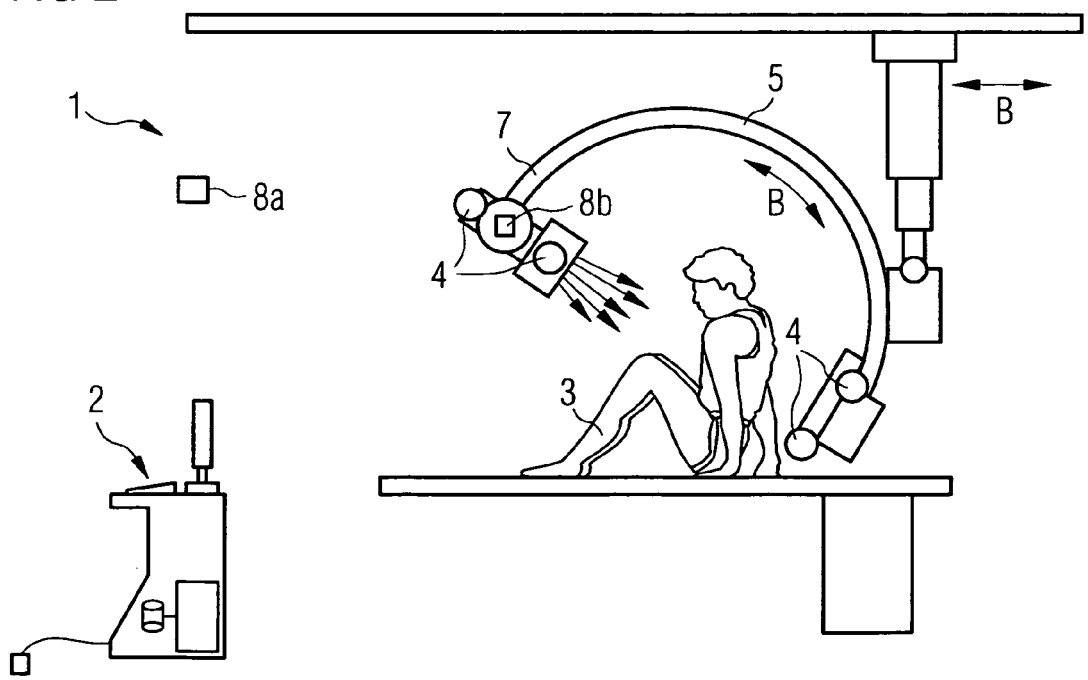
FIG. 2 shows an x-ray C-arm system with corresponding collision sensors according to the present invention.

FIG. 2 shows an x-ray C-arm system, for cardiology or angiography for instance, with sensors 4 on correspondingly exposed points of the x-ray emitter and the x-ray detector. The C-arm can likewise be moved in the movement direction B in a similar manner as the C-arm can rotate about the patient 3. The moveable part 5 is in this case the C-arm 7, which rotates about the patient 3. The distance data of the sensors 4 is transmitted to the control device 2.

According to an advantageous embodiment of the invention, a second sensor 8 detects the respective position of the C-arm 7, in which a second part 8b of the second sensor 8 is attached to the x-ray emitter and corresponding position data is thus transmitted to the first part 8a of the second sensor 8 or directly to the control device 2. Position detectors of this type are known in the prior art, an electromagnetic system is suitable here for instance, with the first sensor part 8a establishing an electromagnetic field, which is correspondingly detected in the second sensor part 8b with the movement of the moveable part 5, so that position changes can be determined.

Figure 3:
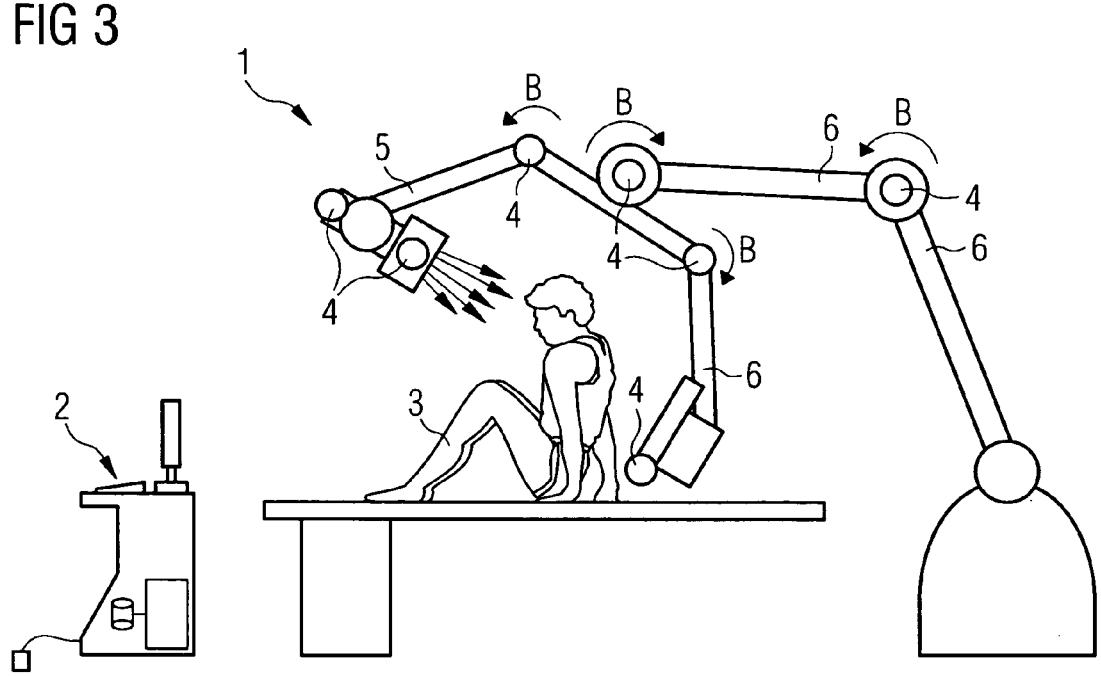
FIG. 3 shows a robot arm system with corresponding collision sensors on exposed points on the moveable arms.

Alternatively, FIG. 3 shows a robot arm system with different rotating arms 6, which can implement different rotating movements B. The rotating movements B are implemented here in all directions, in which the individual rotating arms 6 are linked by ball joints, so that the moveable part can be moved in all six directions of motion. Sensors 4 are also positioned here on exposed points of the moveable part 5 and measure the distance to the patient 3. This data is likewise transmitted to the control device in a wired or wireless manner. The control device 2 controls and/or regulates the individual robot arms 6 in accordance with the distance data of the sensors 4.

The invention claimed is:

1. An anti-collision method for a medical imaging system comprising a moveable part moved about a patient, comprising:
    detecting a surface of an external object by a sensor connected to the moveable part;
    transmitting the detection to a control device;
    calculating a distance between the moveable part and the surface of the external object according to the detection by the control device; and
    controlling a movement of the moveable part based on the calculated distance by the control device to prevent a collision of the moveable part with the external object, wherein a coordinate system calibration between the imaging system and the sensor is performed prior to recording an image data of the patient.

2. The anti-collision method as claimed in claim 1, wherein the external object is the patient or an object of the medical image system.

3. The anti-collision method as claimed in claim 1,
    wherein the sensor detects a position of an individual surface area of the external object and transmits the position to the control device, and
    wherein the control device:
        stores a position of the moveable part or receives the position of the moveable part detected by a second sensor,
        calculates the distance between the moveable part and the individual surface area of the external object from the position of the individual surface area of the external object and the position of the moveable part, and
        controls a speed or a movement direction of the moveable part based on the distance.

4. The anti-collision method as claimed in claim 1, wherein the sensor is an optical sensor.

* * * * *